United States Patent [19]
Singer et al.

[11] Patent Number: 5,214,386
[45] Date of Patent: May 25, 1993

[54] APPARATUS AND METHOD FOR MEASURING PARTICLES IN POLYDISPERSED SYSTEMS AND PARTICLE CONCENTRATIONS OF MONODISPERSED AEROSOLS

[76] Inventors: Hermann Singer, Luettendamm 9, 2000 Stapelfeld/Hamburg; Michael Rossner, Haldesdorfer Strasse 158, 2000 Hamburg 71, both of Fed. Rep. of Germany

[21] Appl. No.: 589,668

[22] Filed: Sep. 28, 1990

[30] Foreign Application Priority Data

Mar. 3, 1990 [EP] European Pat. Off. ........... 90104165

[51] Int. Cl.⁵ ............................................. G01N 27/60
[52] U.S. Cl. .................................... 324/452; 324/71.1
[58] Field of Search ............... 324/452, 464, 457, 71.1

[56] References Cited

U.S. PATENT DOCUMENTS

| | | | |
|---|---|---|---|
| 3,526,828 | 9/1970 | Whitby | 324/464 |
| 3,679,973 | 7/1972 | Smith, Jr. et al. | 324/464 X |
| 4,117,715 | 10/1978 | Hoenig | 324/452 X |
| 4,249,131 | 2/1981 | Owen | 324/452 |
| 4,288,749 | 9/1981 | Martin | 324/464 |
| 4,556,849 | 11/1985 | Kalakutsky et al. | 324/464 |
| 4,685,569 | 8/1987 | Osaki et al. | 324/455 X |
| 4,837,440 | 6/1989 | Burtscher et al. | 324/464 X |
| 4,910,463 | 3/1990 | Williams, II et al. | 324/464 X |
| 4,973,909 | 11/1990 | Castle et al. | 324/452 |

OTHER PUBLICATIONS

M. Rossner, H. Singer, "Measurement of Micrometer Particles by Means of Induced Charges"; 1989 IEEE Industry Applications Society Annual Meeting, IEEE Catalog No. 89CH2792-0.

Primary Examiner—Kenneth A. Wieder
Assistant Examiner—Glenn W. Brown
Attorney, Agent, or Firm—Sixbey, Friedman, Leedom & Ferguson

[57] ABSTRACT

A method and apparatus useful in measuring the size, charge, velocity and concentration of particles in polydispersed systems, and particle concentrations of monodispersed aerosols. A particle flow to be evaluated is conducted through at least one active electric field sensor, which may be constructed in an annular, point, or segmented annular configuration. The charge induced by each particle on the sensor is fed to an active charge amplifier. The output signal of the amplifier serves as input signal for a measured value indicator. The amplifier is a component for a measured value evaluation circuit, which consists of at least one capacitor, one resistor and the amplifier and, which is preferably integrated into the arrangement of the sensor. A computer or microprocessor is used in analyzing the sensor output to determine desired parameters descriptive of the particles and their movement. The particle flow may be charged prior to measurement and the particles may also be separated according to charge.

36 Claims, 7 Drawing Sheets

APPARATUS AND METHOD FOR MEASURING PARTICLES IN POLYDISPERSED SYSTEMS AND PARTICLE CONCENTRATIONS OF MONODISPERSED AEROSOLS

BACKGROUND OF THE INVENTION

The invention relates to a method for measuring the size, charge, velocity, and/or concentration of particles in polydispersed systems and particle concentrations in monodispersed aerosols, and discloses a novel measuring device for performing the process.

It is known to use optical measuring processes to detect particle sizes, particle concentrations and flow velocities, and to optoelectronically convert and display the measured signals. The measuring devices necessary for this purpose are relatively expensive. Also, in these systems, the measuring result is influenced by the optical properties of the particles. In the case of particle sizes smaller than or equal to 0.1 micron, because of the Raleigh scattering effect, an optical measurement becomes more difficult or impossible.

It is further known to use electric field probes for contactless measurement of charge clouds. In view of the fact that aerosol particles are electrically charged, particle size measurements have been made with the use of electric charges, either by integrating the charge of a collecting receptacle or impact disk over time, or by measuring the charging current of the collecting receptacle or impact disk. These processes are limited in their measuring accuracy, and do not make possible any measurement of very low particle concentrations and of flow velocities.

SUMMARY OF THE INVENTION

Therefore, it is an object of the invention to provide a method and apparatus for reliably detecting even individual particles in the range of larger than or equal to 1 micron and particle clouds down to the range of 10 nm.

Another object is to provide a method useful in measuring the size, charge, velocity and concentration of particles in polydispersed systems.

A further object of the present invention is to provide an apparatus useful in measuring the size, charge, velocity and/or concentration of particles in polydispersed systems.

Yet another object of the present invention is to provide a method of measuring particle concentrations of monodispersed aerosols.

Another object of the present invention is to provide an apparatus useful in measuring particle concentrations in monodispersed aerosols.

A more specific object of the present invention is to provide a sensor and signal processing circuitry useful in detecting charged particles by induction.

These objects and others are achieved according to the present invention by providing a method and apparatus useful in measuring the size, charge, velocity and concentration of particles in polydispersed systems, and particle concentrations of monodispersed aerosols, is disclosed. A particle flow to be evaluated is conducted through at least one active electric field sensor, which may be constructed in an annular, point, or segmented annular configuration. The charge induced by each particle on the sensor is fed to an active charge amplifier. The output signal of the amplifier serves as input signal for a measured value indicator. The amplifier is a component for a measured value evaluation circuit, which consists of at least one capacitor, one resistor and the amplifier, and which is preferably integrated into the arrangement of the sensor. A computer is used in analyzing the sensor output to determine desired parameters descriptive of the particles and their movement. The particle flow may be charged prior to measurement and the particles may also be separated according to charge.

BRIEF DESCRIPTION OF THE DRAWINGS

FIG. 1b is an alternative active $\dot{D}$ sensor which may be used with the circuit of FIG. 1a;

DETAILED DESCRIPTION OF THE PREFERRED EMBODIMENTS

Figure 1A:
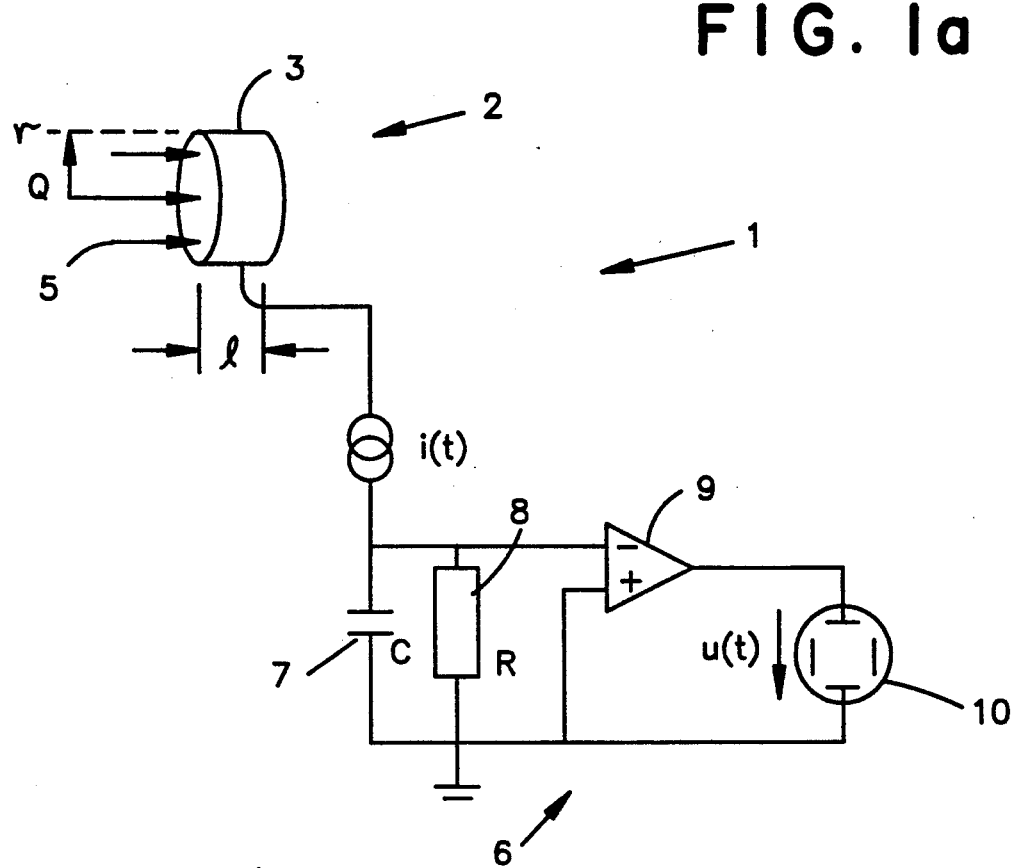
FIG. 1a is a circuit diagram showing an active $\dot{D}$ sensor of the measuring device of the present invention.

The present invention relates to a method for measuring the size, charge, velocity, and/or concentration of particles in polydispersed systems and the particle concentration of monodispersed aerosols and also provides a novel apparatus useful in practicing the method.

To understand the method and apparatus of the present invention, it is necessary to discuss briefly the theory behind the particle detection and evaluation methods of the invention. The natural charging of particles is indeed of a strongly stochastic nature, but it is nevertheless possible to determine a relationship between particle charge and particle size by statistical methods. At a well-defined charge, a charge-size relation clearly exists and can be described for spherical particles with charging mechanisms known from electrofilter physics. Each particle has a field charge and a diffusion charge. Both charging mechanisms can be added together and the sum is the total charge of the particle. The field charge of a particle is given by:

$$Q_p = 4\pi\epsilon_0 R^2 \cdot E \cdot \left[ 2\frac{\epsilon_p - 1}{\epsilon_p + 2} + 1 \right] \cdot \frac{t}{t + \tau} \quad (1)$$

$$\text{where } \tau = \frac{4\epsilon_0}{Neb}$$

while the diffusion charge of the particle is given by:

$$Q_p = \frac{4\epsilon_o RkT}{e} \cdot \left[ \ln\left( \frac{RNe^2 \cdot v_i}{4\pi\epsilon kT} \cdot t + 1 \right) \right] \quad (2)$$

where:
- $Q_p$ = particle charge
- $R$ = equivalent particle radius
- $\epsilon_o$ = dielectric constant of the carrier gas
- $\epsilon_p$ = dielectric constant of the particle
- $N$ = ion concentration
- $e$ = elementary charge
- $b$ = ion mobility
- $K$ = Boltzmann constant
- $v_i$ = ion velocity
- $t$ = time.
- $T$ = absolute temperature Field charge is dominant for particles with diameters greater than about 1 micron, while diffusion charge is dominant for smaller particles. According to the present invention, the charge of the particles can be measured without contacting the particles using $\dot{D}$ sensors according to the present invention. A $\dot{D}$ sensor measures the temporal change in charge. Particles being electrically charged induce an electric "counter-charge" at the $\dot{D}$ sensor which is measured and amplified. Using an integrating circuit, the output signal can be integrated. At the output, a time varying voltage signal $U(t)$ is obtained, and used as an input signal for a computer or other device.

The $\dot{D}$ sensors according to the present invention are constructed by connecting a metal foil plate or plates to a lead or leads which are monitored to detect charge fields. The metal foil plate or plates are preferably attached to non-conductive support structures. For example, the foil may be attached to the inside surface of a plastic or fiberboard tube. In some cases it will also be desirable to place a relatively thin insulating coating over the foil.

The principles of operation of the $\dot{D}$ sensor of the present invention will be described generally herein. A more complete description of the operation principles of the system is contained in the inventors' paper, "Measurement of Micrometer Particles by Means of Induced Charges," presented at the 1989 IEEE Industry Applications Society Annual Meeting, IEEE catalog number 89CH2792-0, which is incorporated herein by reference.

The integrated signal of the $\dot{D}$ sensor is proportional to induced charge $Q^*$, for which the following relations are true:

$$i(t) = \frac{dQ^*}{dt} = \epsilon A \frac{dE}{dt} \quad (3)$$

$$u(t) = \quad (4)$$

$$\frac{1}{C} e^{-\frac{t}{RC}} \left[ Q^*(t) e^{-\frac{t}{RC}} - \frac{1}{RC} \int_0^t Q^*(\tau) e^{-\frac{\tau}{RC}} d\tau \right]$$

$$C \to \infty: u(t) = \frac{Q^*}{C}; \; RC \to 0: u(t) = R \cdot \frac{dQ^*}{dt} \quad (5)$$

Figure 1B:
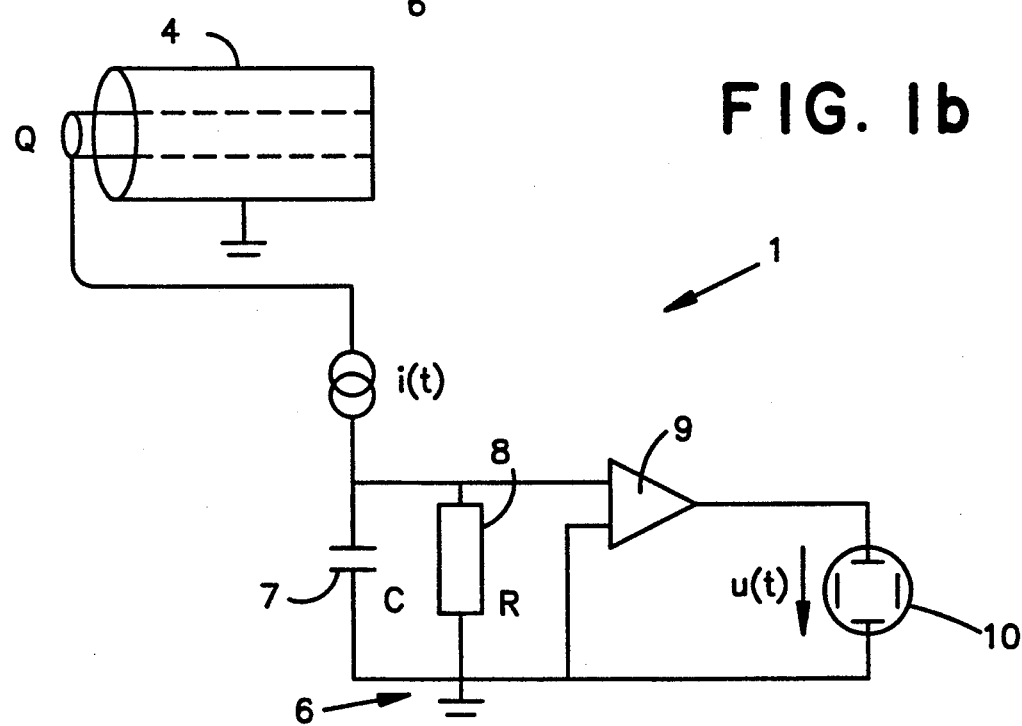

In FIGS. 1a and 1b, different embodiments of active $\dot{D}$ sensors 2 are shown. In FIG. 1a, a measuring circuit 1 is shown comprising electric measured value evaluation circuit 6, and active $\dot{D}$ sensor 2. As a function of the respective problem different active $\dot{D}$ sensors 2 can be used. For the detection of individual small particles, as are present in Clean rooms, for example, annular D sensors 3 are suitable, and the $\dot{D}$ sensor 2 shown in FIG. 1a is an annular $\dot{D}$ sensor 3. The annular $\dot{D}$ sensors 3 surround the air stream to be analyzed, and thus make possible a good charge use of the field-generating particles.

As shown in FIG. 1b, a $\dot{D}$ point sensor 4 can be constructed by locating a circular piece of metal foil in an air stream and attaching measuring leads thereto. $\dot{D}$ point sensors 4 are used if the detection is to be in only a specific area of an air stream.

The output of $\dot{D}$ sensors 2 is processed by measured value evaluation circuit 6. Measured value evaluation circuit 6 consists of a capacitor 7 with a specific capacity, ohmic resistance 8, an amplifier 9 and a measured value indicator 10. But it is also possible to provide several electric components such as capacitors 7 or ohmic resistances 8 in measured value evaluation circuit 6.

Figure 2:
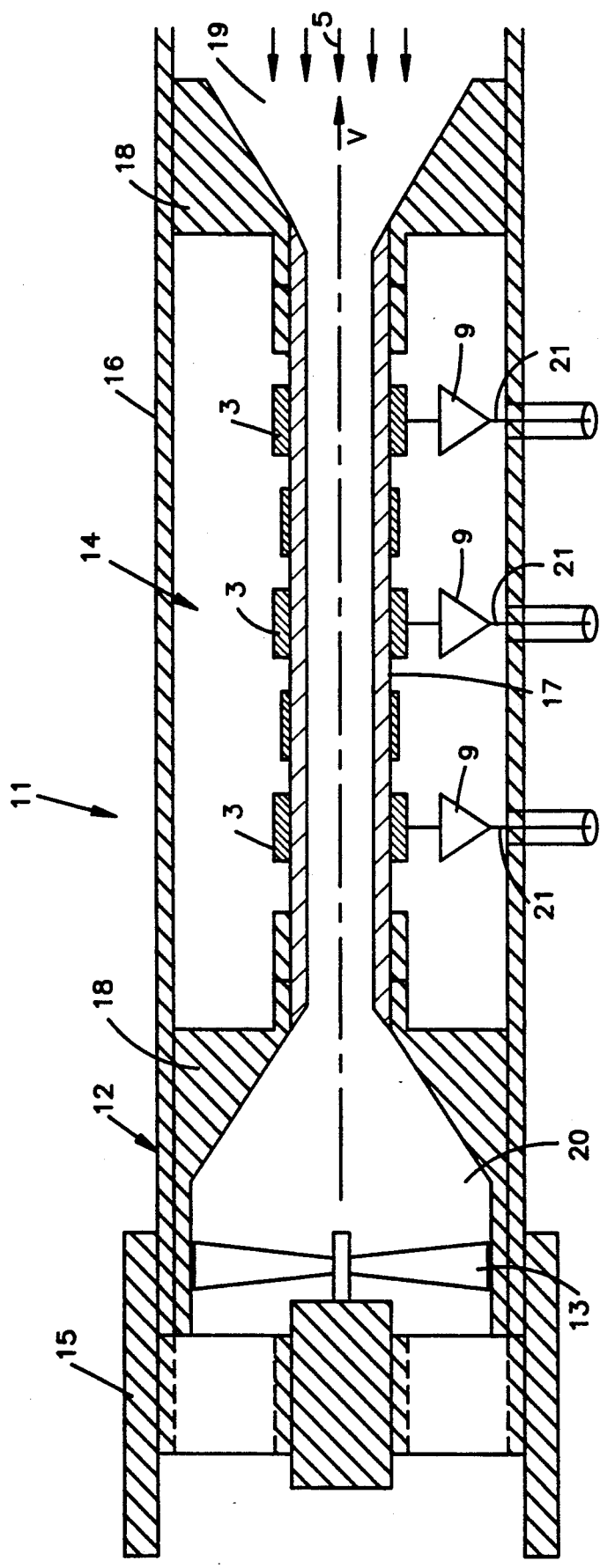
FIG. 2 is a side sectional view of a sensor unit of the measuring device of the present invention.

FIG. 2 shows a sensor unit 11, which is used for individual particle measurement. Sensor unit 11 consists of a tubular housing 12, in which an axial-flow fan 13 and sensor device 14 are placed. Axial-flow fan 13 is in a tubular jacket housing 15, in which a jacket pipe 16 for receiving sensor device 14 is provided on the suction side of the axial-flow fan 13. A measuring pipe 17, made, for example, of plastic, is coaxially disposed in jacket pipe 16. Holding pieces 18 connect the measuring pipe 17 to both end sections of the jacket pipe 16. Housing 12 is designed as a shield. Sensor device 14 is prevented from being influenced by unwanted signals by the shield.

The intake side holding piece 18 has a conical inlet 19 and the discharge side holding piece 18 has a conical outlet 20. Sensor device 14 consists of three annular $\dot{D}$ sensors 3, which are placed at a distance from one another on measuring pipe 17. Each annular $\dot{D}$ sensor 3 is connected to an amplifier 9, whose outlet is connected to measured value indicator 10 by a measured value pipe 21 that extends through jacket pipe 16. At least one capacitor 7 and one ohmic resistance 8 is connected between each amplifier 9 and related annular probe 3. To reduce polarization effects in the amplifier supply line, amplifier 9, capacitor 7 and ohmic resistance 8 are integrated close to the sensor in the arrangement between measuring pipe 17 and the inside wall of jacket pipe 16.

Sensor unit 11 can be used for charge measurement of individual small particles, as are present in clean rooms. Axial-flow fan 13 intakes air to be analyzed by measuring pipe 17, on which annular $\dot{D}$ sensors 3 are located. The particle charge induced on an annular D sensor 3 is fed to an active amplifier 9 associated with the $\dot{D}$ sensor 3 by means of capacitor(s) 7 and ohmic resistance or resistances 8 (as shown in FIG. 1a) to keep the unwanted effects of the measuring supply line small.

Optimal charge use is achieved by optimized annular $\dot{D}$ sensors 3, which are constructed so as to have the greatest possible local resolution and very short response time. This is achieved by providing $\dot{D}$ sensors 3 constructed with small lengths of foil. Preferably, in the case of annular $\dot{D}$ sensors 3 as shown in FIG. 1a, the ratio of the length l of the $\dot{D}$ sensor 3 to the radius r is less than 1. To achieve a high signal-noise ratio the signal is further amplified by signal-matched filters. To make possible the use of matched filters for noise suppression, it is advantageous to design approximately constant flow velocities in the pipe to guarantee known and determined sensor signals at occurring individual events. The signals of all three annular $\dot{D}$ sensors 3 are appropriately integrated in a time-delayed manner. With this arrangement of annular $\dot{D}$ sensors 3 a sensitivity can be achieved which corresponds to an equivalent charge noise of $Q_{eff}$=0.034 fC. Thus, individual particle charges of 0.13 fC can be detected with sufficient accuracy. A further improvement of the signal-to-noise ratio is possible by correlation of the sensor signals.

If necessary, the particles of particle stream 5, entrained in the air stream, are also electrically charged by a charging device which ionizes the air upstream of the intake into measuring pipe 17. Such a charging device is shown in FIG. 3 and is described later in greater detail.

The volume of air to be analyzed by sensor unit 11 can be up to 0.1 $m^3$/sec with the appropriate diameter of measuring pipe 17, which means a marked improvement of the analysis time or the analysis volume in comparison with known optical processes. A matching of sensor unit 11 to higher pollutant concentrations can take place by a mechanical reduction of the measuring pipe diameter. Because of the low material prices and the slight sensitivity in comparison with optical processes, this sensor unit 11, designed as a particle counter, is especially suitable for measurements in clean rooms of a lower cleanliness standard, and also for measurement of the dust load in industry and work spaces. The contactless measurement of the flow velocities in a pipe or the measurement of the volume flow in the pipe by annular $\dot{D}$ sensors 3 can also be performed with sensors that do not completely surround the pipe. The average flow velocity can be determined with knowledge of the sensor distance by measurement of the time lag of the individual signals or by correlation of at least two sensor signals in each case. In this case ions, electrons or charged dust particles entrained in the air stream can be used for signal generation, to the extent that they follow the air stream without slippage.

Figure 3:
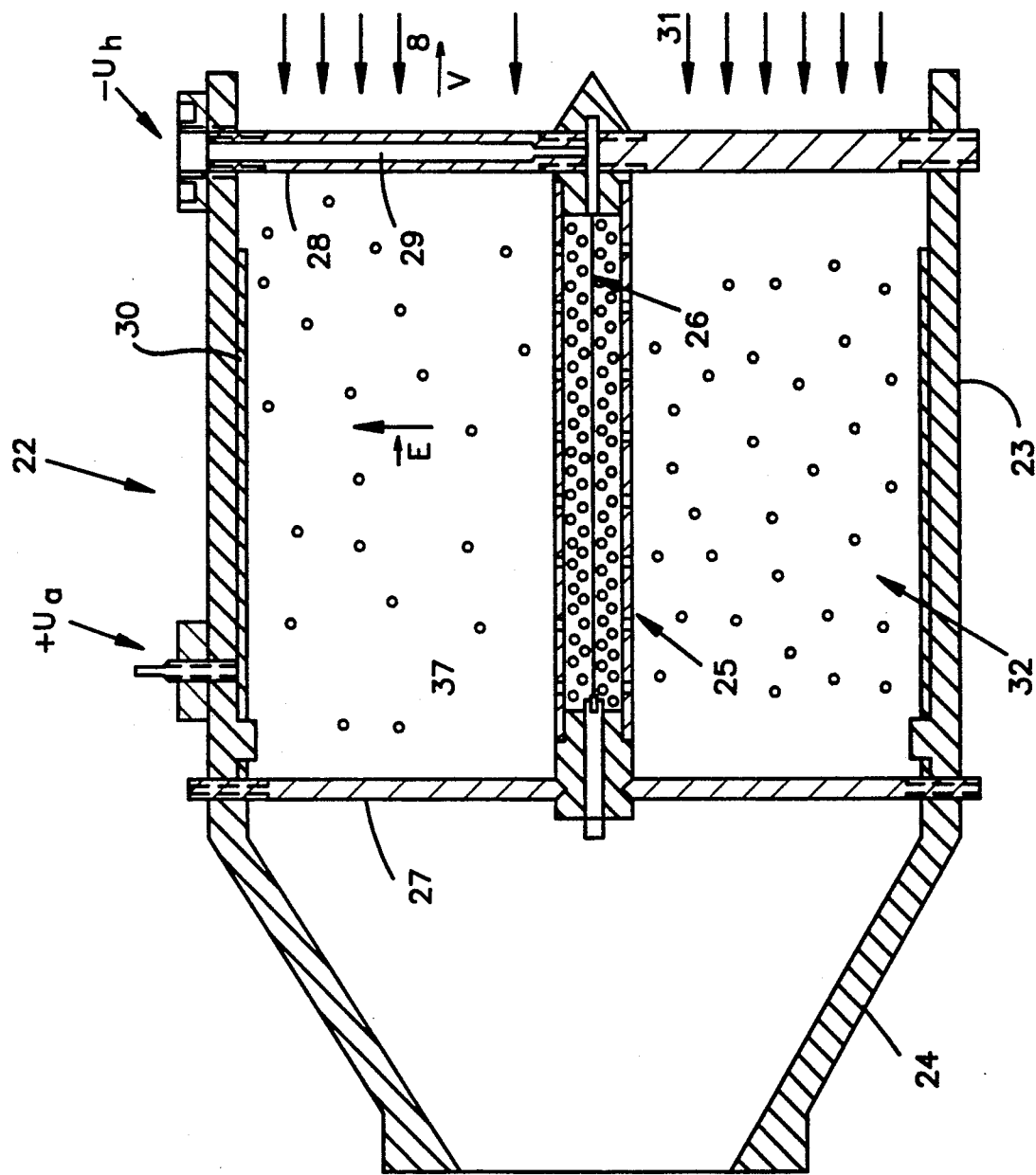
FIG. 3 is a side sectional view of a charging device of the measuring device of the present invention.

Referring now to FIG. 3, charge device 22, which is used to ionize the intake air and thus charge the particle stream 5, is shown in detail. Charge device 22 consists of a cylindrical jacket 23, which on the discharge side is connected to a connecting piece 24 that tapers in cross section in the flow direction. A sensor unit 11, as shown in FIG. 2, can be connected to the connecting piece 24. Charging device 22 has a coaxial three-electrode arrangement, which makes possible a separate adjustment of the ion stream density and electric field in the particle-laden air stream. For this purpose, a grating pipe 25 with a center emission electrode 26 is placed coaxially in jacket 23. Grating pipe 25 is connected to jacket 23 by spacers 27, 28. A line 29, by which emission electrode 26 is applied to a negative voltage $-U_h$, is run in spacer 28. A continuous anode 30, which is connected to a positive anode voltage source $+U_a$, is placed on the inside surface of jacket 23.

Both the density of the volume charge and the electric field strength in the entire flow duct are determined by the anode current and anode voltage. Particles 37, entrained in air stream 31, are electrically charged in the ionized air produced by charging device 22. Charging device 22 produces ions by corona discharge in the vicinity of emission electrode 26 lying on the negative high-voltage potential. If a positive anode voltage is applied, the ions drift from the inside of grating pipe 25 into flow duct 32 between jacket 23 and grating pipe 25 and, according to equations (1) and (2) discussed previously, accumulate on particles 37 entrained in air stream 31. Because of the coaxial geometry of the arrangement, a homogeneous electric field at known space charge ratios can be achieved in flow duct 32. Thus, according to equations (1) and (2), a known relationship between the spherical particle radius and the charge results. At a charge field strength of 2 kV/cm, corresponding to the detection limit of 0.13 fC, particles of about 2 microns in equivalent diameter can be detected.

In the described charge devices 22 the particles may be provided with well-defined electrical charges by small ion accumulation. For this purpose, a high dc voltage can be applied to the respective anode 30 as voltage $U_a$. But it is also possible to superpose an ac voltage on this dc voltage or use a dc voltage with an added pulse voltage.

If the measurement is not limited only to individual particles 37, by the total or space charge of electrically charged aerosol particles, a determination can also be made of the grain size distribution and concentration of aerosols with particle diameters down to 10 nanometers in concentrations of $10^{14}$–$10^6$ parts/$m^3$. These conclusions are reached by applying two main principles: First, the particle charge, which results here substantially by the accumulation of small ions because of the diffusion processes, both with respect to its total charge and its time charge ratio is dependent on the particle radius, as described by equation (2). Second, the separation of these charged aerosol particles from an air stream, because of the forces of an outside electric field, also depends on the particle diameter.

To determine the grain size distribution and concentrations, a measuring arrangement 33 can be used, as shown in FIG. 4. Measuring arrangement 33 consists of a sensor unit 11, a separation unit 35 and a charging device 22, which are connected to a computer or microprocessor 36. Computer 36 controls the measuring process and performs the measured value evaluation. Sensor unit 11 consists of an axial-flow fan 13 and a sensor device 14. Annular Ḋ sensors 3 are each connected on the discharge side with an amplifier 9 as described previously with reference to FIG. 2. If the aerosol particles, after they have passed through charging device 22, are exposed to a well-defined electric field in separation unit 35 and the remaining space charge is measured with sensor unit 11 with variation of the charge and separation conditions, statements can be made on the concentration and size of measured particles 37.

The electric field in separation unit 35 separates the particles depending on their charge, which is related as described previously to the size of the particles. Particles 37 with diameters smaller than 10 microns follow almost slip-free slow air streams (with velocity between 0 and 20 m/sec). If the signals of two closely adjacent annular Ḋ sensors 3, which surround a pipe that particles flow through, are correlated, the average flow velocity in this pipe can be determined. The average flow velocity can also be determined by calculating the time lag in the signals if the particles do not slip in the air stream.

By using small annular Ḋ sensors 3 with low flow resistance, flow profiles—compared with the sensor measurements—can also be determined in large flow ducts such as in smokestacks and air shafts. A prerequisite is that a marked main flow direction exists in the flow duct.

If sufficient field-generating particles 37 are not present in the flow, it is possible to provide for sufficient charge amounts either by addition of fumes such as, for example, cigarette smoke, or by introduction of an ionization source at a sufficient distance ahead of annular $\dot{D}$ sensor 3. On the other hand, with large annular sensors (as shown in FIG. 1b), which, e.g., are placed around a smokestack or air shaft, or with point sensors, integral determinations can also be made of the particle count or concentration in the total detected flow cross section. It is particularly advantageous that the described processes can be used where the flow is highly concentrated and optically impermeable so that optical sensors are not effective.

Figure 5:
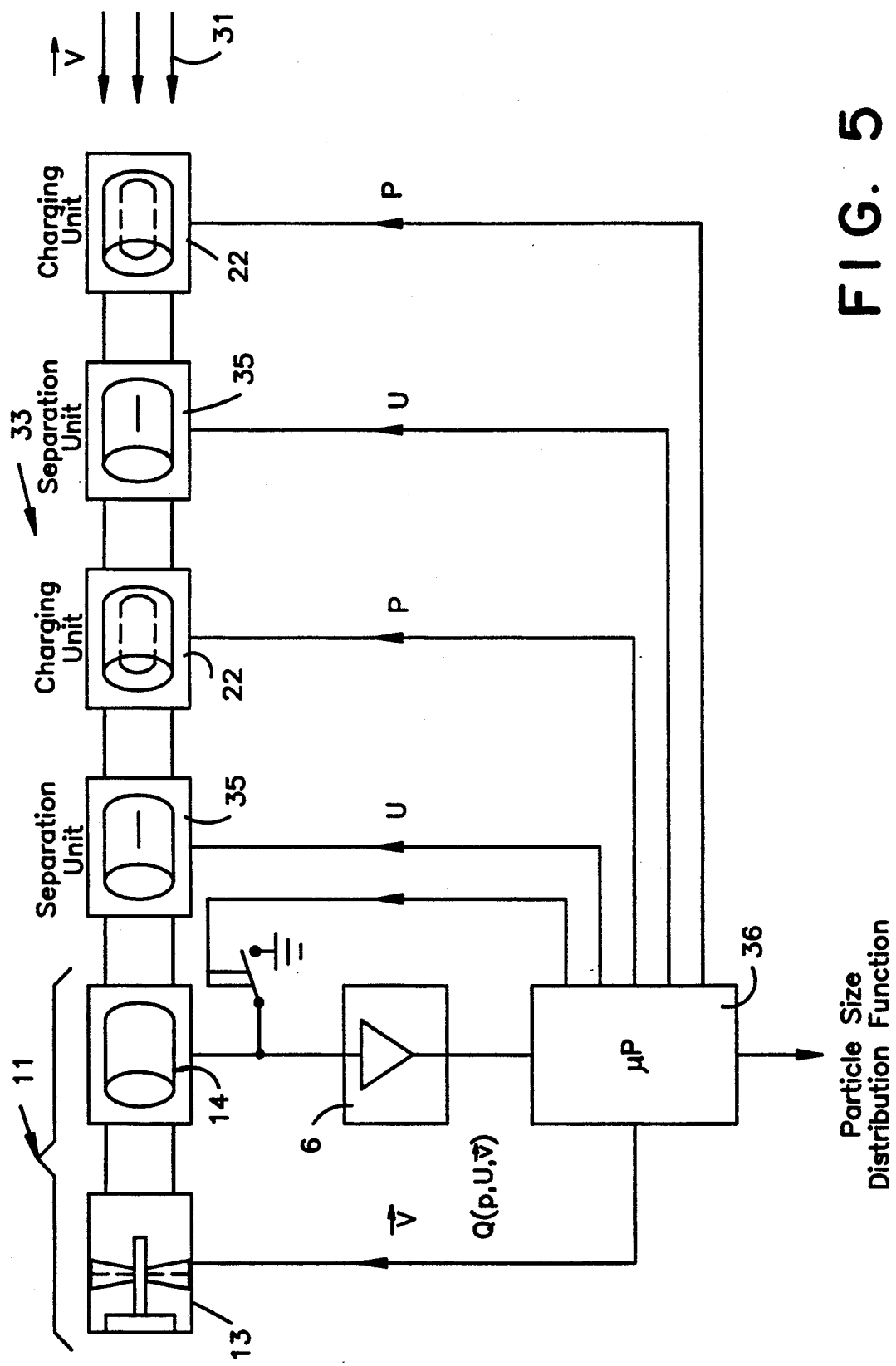
FIG. 5 is a block diagram of an alternative embodiment of a measuring device for aerosol measurement according to the present invention.

FIG. 5 shows a further embodiment of a measuring arrangement 33 according to the present invention. For improvement of the grading, e.g., in the grain size range from 10 nm to 500 nm two charging units 22 with different ionization strengths and two separation units 35 are consecutively connected in the air/particle stream and also connected with computer 36 for control and monitoring. Any number of charge units 22 and separation units 35 can be consecutively connected if desired. Using this arrangement, the computer can determine a particle size distribution function as a function of the sensing means output.

Figure 6:
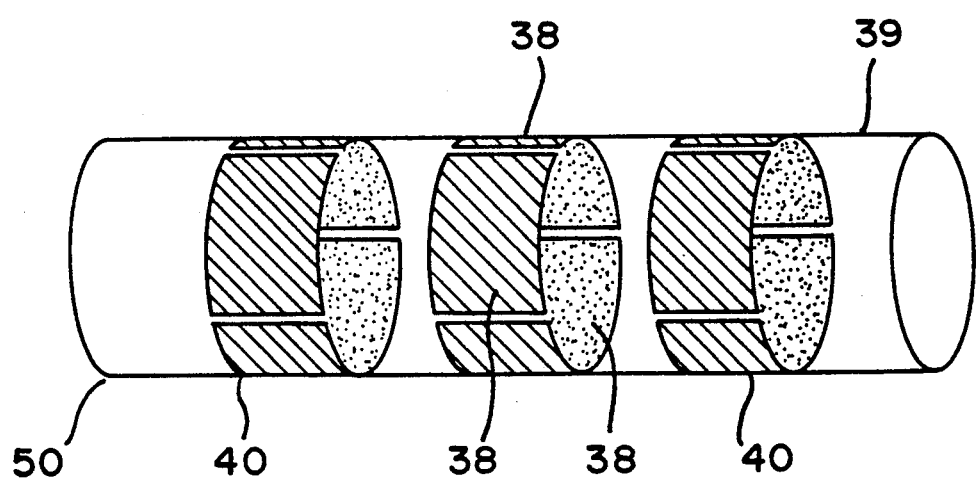
FIG. 6 is a perspective view of a segmented annular $\dot{D}$ sensor of the measuring device of the present invention.

Referring now to FIG. 6, a segmented annular $\dot{D}$ sensor unit 50 is shown. The segmented annular $\dot{D}$ sensor unit 50 comprises a plastic tube 39 and three segmented annular $\dot{D}$ sensors 40. Each segmented annular $\dot{D}$ sensor 40 is made up of three sensor segments 38 which are preferably of thin metal foil The sensor segments 38 are preferably separated from one another along lines parallel to the central axis of the plastic tube 39. The plastic tube 39 provides structural support for the sensor segments 38 of annular $\dot{D}$ sensors 40. While plastic is the preferred material for plastic tube 39, other insulating materials such as paperboard, etc. could also be used. By using several segmented annular $\dot{D}$ sensors 40, it is possible to determine the spatial location of a charge. By segmenting of the $\dot{D}$ sensors 40 in this manner, the position of a charge or charge accumulation in a pipe 39 can be clearly determined. Therefore, this process can also be used for locating particle accumulations in a pipe flow. Also with two additional adjacent, segmented annular $\dot{D}$ sensors 40 in connection with the above-mentioned correlation process, differential determinations can also be made regarding the flow profile of a pipe flow. Each annular sensor element 38 will be connected to a sensor circuit arrangement with at least one capacitor 7 and an ohmic resistance 8 with an amplifier 9, as disclosed in previously described embodiments of the invention.

Figure 4:
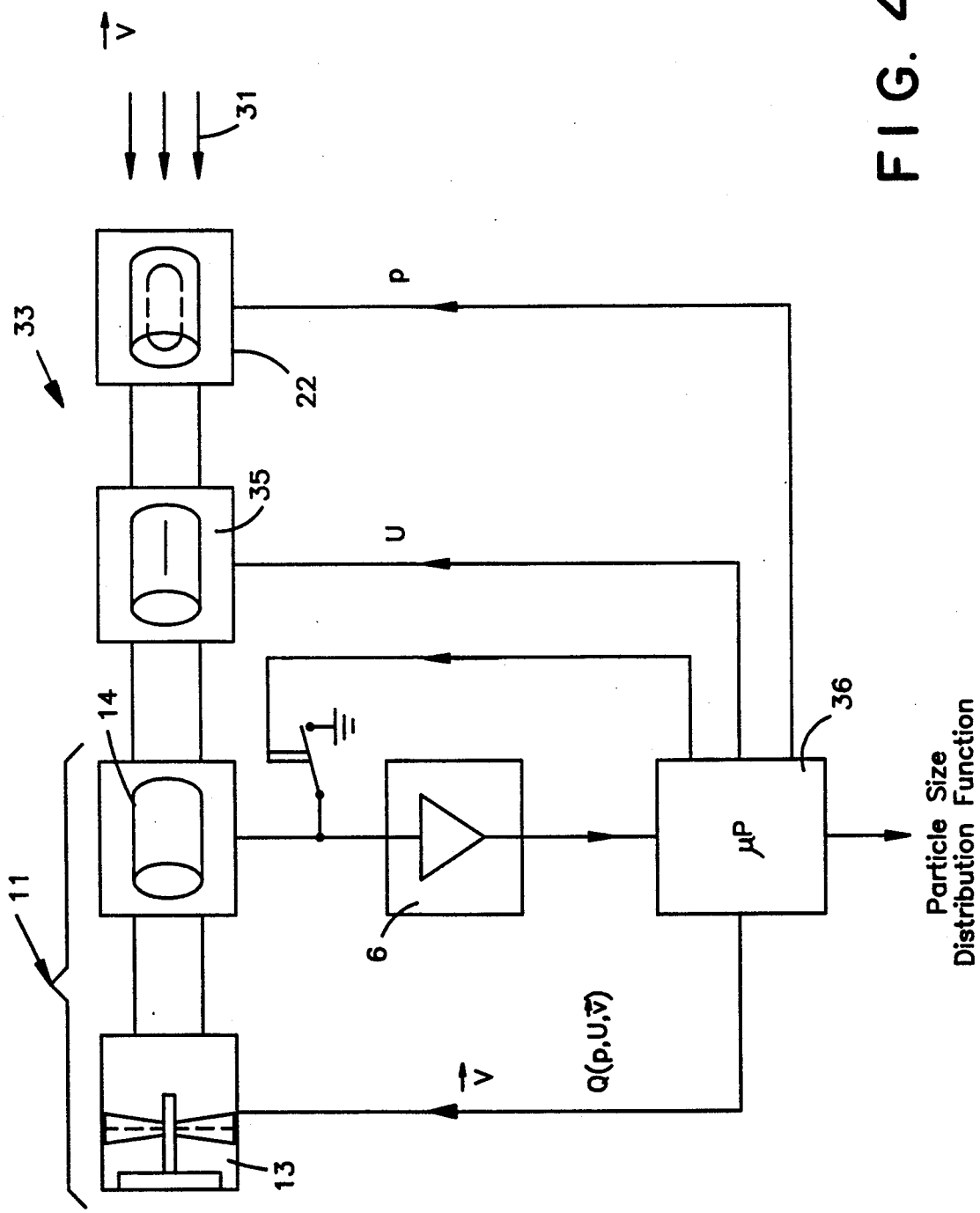
FIG. 4 is a block diagram of a measuring device for aerosol measurement according to the present invention.
Figure 7:
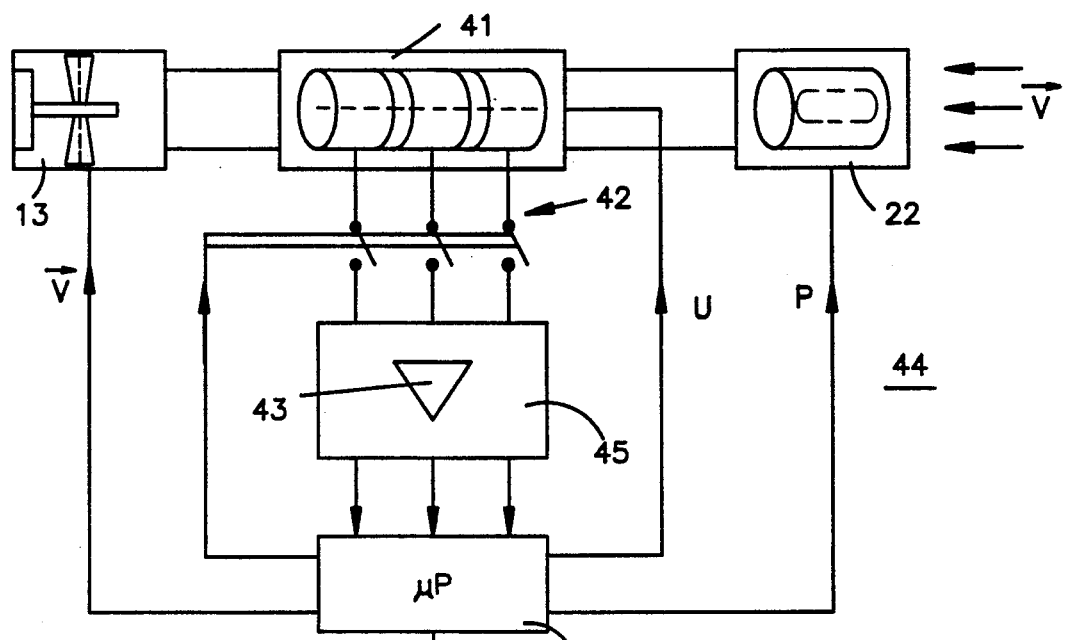
FIG. 7 is a block diagram of an alternative embodiment of the measuring arrangement for aerosol measurement.
Figure 8:
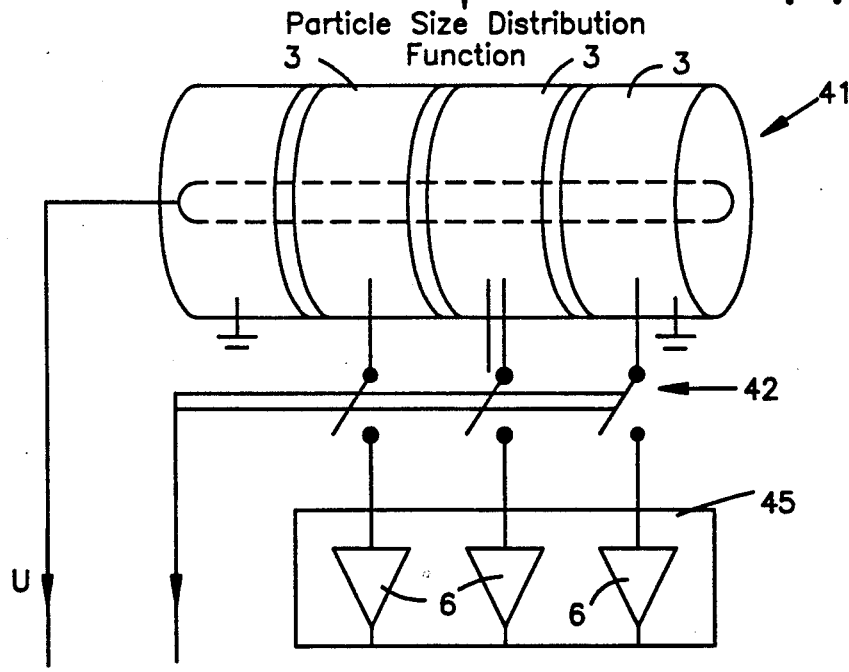
FIG. 8 is an enlarged detailed view of the measuring arrangement according to FIG. 7.

FIG. 7 shows a measuring arrangement which provides improved sensitivity and grading of particles in the subnanometer range, when compared with the measuring arrangements 33 shown in FIGS. 4 and 5. Sensor device 14, formed from consecutive annular $\dot{D}$ sensors 3 (as shown in FIG. 2), is integrated into a separation unit 35 (as shown in FIG. 4) so that a component 41, unified in itself, is formed. This component 41 is placed between an axial-flow fan 13 and a charging device 22.

As in the above-described process of aerosol analysis, here also the aerosol particles (10 nm–500 nm) are taken in by axial-flow fan 13 and electrically charged in charging device 22. But in contrast with the embodiments described with reference to FIGS. 4 and 5, the induced charge of the separated particles is now measured. These particles separate during the separation process at different positions, corresponding to their migration velocity under the influence of the electric field. If the separation process ends, particles of known size, whose charge can be determined with a measuring device 45, are on annular Ḋ sensors 3.

According to the relations between particle charge and particle size given by equation (2), the number of particles contained in the intake air stream can be determined. Annular Ḋ sensors 3 thus act as separation electrodes of component 41. As a function of the respective axial position of annular Ḋ sensors 3, a determined narrowly limited particle size spectrum is achieved on the individual sensor surfaces. To avoid the complete discharge of the separated particles, an insulating coating can be placed on or above annular Ḋ sensors 3.

Measuring device 45 consists of measured value evaluation circuits 6 (shown in FIG. 1*a*), which are provided for each annular Ḋ sensor 3 each of component 41. These measured value evaluation circuits 6 can be turned on or off with switches 42, placed between capacitors 7 and resistances 8 of measured value evaluation circuits 6. Measuring device 45 is inactive during the separation process and is activated after completion of the separation process to determine the surface charge on annular Ḋ sensors 3.

It is possible to combine the individual amplifiers 9 of the individual measured value evaluation circuits 6 into one amplifier unit 43. Alternatively, it is also possible to perform a serial interrogation by multiplexing signals from individual Ḋ sensors into only one amplifier 9.

While various embodiments in accordance with the present invention have been shown and described herein, numerous other changes and variations will be recognized, by those of ordinary skill in the art, to be possible in accordance with the present invention. Thus, the present invention should not be viewed as being limited to the embodiments and features thereof as described herein, and instead, should be viewed as encompassing the full scope of the appended claims.

We claim:

1. A method for measuring any of the size, charge, velocity and concentration of particles in polydispersed systems, and particle concentrations of monodispersed aerosols, including the steps of:

conducting the particle flow through at least one active field sensor operating by induction;

measuring charges of electrostatic induction of particles passing the sensor as inducted on the active field sensor and transmitting the resulting measurement of induction for each particle passing the sensor to an active charge amplifier which provides an output signal; and transmitting the output signal of the active charge amplifier to a measured value indicator;

wherein said steps are performed so as to contactlessly measure the size and charge of individual electrostatically charged particles in polydispersed systems down to equivalent particle diameters of about 1 micron, whereby charges of particles are determined from the pulse magnitude of said amplified output signal.

2. The method of claim 1, wherein the particle flow is conducted through a pipe with approximately constant flow velocity over the cross section of the pipe, and the charges induced by the particles on at least two annular sensors consecutively placed in the flow and protected from outside electric fields are transmitted to the charge amplitude, and thereafter the signals of several annular sensors are correlated to achieve a high signal-to-noise ratio.

3. The method of claim 2, whereby the signals of the annular sensors are amplified by one amplifier each.

4. The method of claim 1, wherein said steps are performed so as to determine the local flow velocities, signals of active sensors located in the area of a pronounced main flow are correlated on the basis of charges induced on the sensors by the particles.

5. The method of claim 1, wherein the particle flow is conducted through a pipe with approximately constant flow velocity over the cross section of the pipe, and the charges induced by the particles on at least one annular sensor placed in the flow and protected from outside electric fields are transmitted to the charge amplifier, and thereafter the signals of several annular sensors are correlated to achieve a high signal-to-noise ratio.

6. A method for measuring any of the size, charge, velocity and concentration of particles in polydispersed systems, and particle concentrations of monodispersed aerosols, including the steps of:
conducting the particle flow through at least one active field sensor operating by induction;
measuring charges of electrostatic induction of particles passing the sensor as induced on the active field sensor and transmitting the resulting measurement of induction for each particle passing the sensor to an active charge amplifier which provides an output signal; and
transmitting the output signal of the active charge amplifier to a measured value indicator;
wherein said steps are performed so as to measure the particle concentrations of monodispersed aerosols at a grain size range from about 10 nm to about 500 nm at concentrations from about $10^{14}$ to about $10^6$ parts/$m^3$, wherein the aerosol particles are electrically charged by a diffusion charging process and the charge thereof is discharged by electrostatic induction to active D sensors used to measure said charge.

7. A method for measuring any of the size, charge, velocity and concentration of particles in polydispersed systems, and particle concentrations of monodispersed aerosols, including the steps of:
conducting the particle flow through at least one active field sensor operating by induction;
measuring charges of electrostatic induction of particles passing the sensor as induced on the active field sensor and transmitting the resulting measurement of induction for each particle passing the sensor to an active charge amplifier which provides an output signal; and
transmitting the output signal of the active charge amplifier to a measured value indicator;
wherein said steps are performed so as to measure the particle concentration in polydispersed systems in the grain size range from about 10 nm to about 500 nm at concentrations from about $10^{14}$ to about $10^6$ parts/$m^3$ based on particle separation of charged aerosol particles in the polydispersed system dependent on particle size, by action of electric field forces with variation of the separation and charging conditions, wherein simultaneous remaining space-charge is measured by active D-sensors to determine the particle size distribution and concentration of the aerosol.

8. The method of claim 7, wherein the particle flow is conducted through a plurality of charging devices for ionization and through a plurality of separation devices.

9. The method of claim 8, wherein the particles are separated prior to being sensed by the active sensor by the influence of electric field strengths.

10. A method for measuring any of the size, charge, velocity and concentration of particles in polydispersed systems, and particle concentrations of monodispersed aerosols, including the steps of:
conducting the particle flow through at least one active field sensor operating by induction;
measuring charges of electrostatic induction of particles passing the sensor as induced on the active field sensor and transmitting the resulting measurement of induction for each particle passing the sensor to an active charge amplifier which provides an output signal; and
transmitting the output signal of the active charge amplifier to a measured value indicator;
wherein the particle flow is conducted through a pipe made of electrically highly insulating material and electrostatic charges of the particles are induced on at least one annular sensor at the circumference of the pipe.

11. The method of claim 10, wherein the particles of the particle flow are electrically charged in ionized air before entering into the pipe.

12. The method of claim 11, wherein the particles are electrically charged by applied high dc voltage.

13. The method of claim 11, wherein the particles are electrically charged by superposition of dc and ac voltage.

14. The method of claim 11, wherein the particles are electrically charged by superposition of dc and pulsed voltage.

15. The method of claim 10, wherein, for measuring flow distributions, the charges of the particles are induced on a plurality of annular sensor segments making up the annular sensors.

16. The method of claim 10, wherein, for determining the location of particle accumulations in a pipe, the charges of the particles are induced on annular sensor segments of the annular sensors.

17. A method for measuring any of the size, charge, velocity and concentration of particles in polydispersed systems, and particle concentrations of monodispersed aerosols, including the steps of:
conducting the particle flow through at least one active field sensor operating by induction;
measuring charges of electrostatic induction of particles passing the sensor as induced on the active field sensor and transmitting the resulting measurement of induction for each particle passing the sensor to an active charge amplifier which provides an output signal; and
transmitting the output signal of the active charge amplifier to a measured value indicator;
wherein, for measuring the flow velocity of a particle flow in a pipe, ions, electrons or charged dust particles entrained without slippage in an air stream are used for signal generation; wherein signals of two annular sensors placed at a distance from each other are measured; and wherein average flow velocity is then determined from a time lag of individual signals.

18. A method for measuring any of the size, charge, velocity and concentration of particles in polydispersed systems, and particle concentrations of monodispersed aerosols, including the steps of:

conducting the particle flow through at least one active field sensor operating by induction;

measuring charges of electrostatic induction of particles passing the sensor as induced on the active field sensor and transmitting the resulting measurement of induction for each particle passing the sensor to an active charge amplifier which provides an output signal; and transmitting the output signal of the active charge amplifier to a measured value indicator;

wherein, for measuring the flow velocity of a particle flow in a pipe, ions, electrons or charged dust particles entrained without slippage in an air stream are used for signal generation; wherein signals of two annular sensors placed at a distance from each other are measured; and wherein average flow velocity is then determined from the correlation of at least two sensor signals.

19. A measuring device for measuring electric field charges induced by charged particles, comprising:

sensing means including at least one sensing electrode on which a charge is induced by the proximity of a charged particle and mounted on a tubular housing; and measured value evaluation means connected to the sensing means for processing the signal of the sensing means to produce an output indicative of a property of the charged particles, the measured value evaluation means including at least one capacitor, at least one resistor, at least one amplifier and at least one measured value indicating means for indicating a property of the charged particles, and further including a charging means for modifying the charge on particles placed at an inlet of the sensing means for defining a charge on particles independent of place, the charging means further including a charging device having three coaxially-arranged electrodes.

20. The device of claim 19, wherein at least one capacitor, at least one resistor, and at least one amplifier are integrated into the device in a manner reducing polarization effects in an amplifier supply line closer to the sensor.

21. The device of claim 19, wherein the charging means is a plurality of charging units with different ionization strengths that are placed in the particle flow path.

22. The device of claim 19, wherein the charging device consists of a cylindrical jacket in which a grating pipe with an emission electrode is mounted coaxial to the center axis, and wherein, on the inside wall of the cylindrical jacket, a continuous anode is placed to which is applied a voltage.

23. The device of claim 19, wherein the tubular housing has a plurality of annular sensors spaced apart along the central axis thereof, with measuring outputs of the annular sensors each connected to an amplifier.

24. The device of claim 23, wherein at least one capacitor associated with an annular sensor is placed between the measuring pipe and an inside wall of the tubular housing.

25. The device of claim 23, wherein the tubular housing is provided with shielding means for shielding the sensing means from outside electric fields.

26. The device of claim 23, wherein each annular sensor comprises at least three annular sensor segments, each of which is connected to an amplifier.

27. The device of claim 26, wherein a capacitor and a resistor are placed between each annular sensor segment and the associated amplifier.

28. The device of claim 23, wherein at least one capacitor associated with an annular sensor and resistor is placed between the measuring pipe and an inside wall of the tubular housing.

29. The device of claim 19, wherein at least one separation means for separating particles according to the charges thereon is placed between the sensing means and the charging means.

30. The device of claim 29, wherein the separation means comprises a plurality of separation units consecutively placed in the flow direction of the particle flow.

31. The device of claim 29, wherein the sensing means, the separation means, and the charging means are connected to computing means so that the axial-flow fan means, the separation means, and the charging means are all controlled by the computing means to determine a particle size distribution function as a function of the sensing means output.

32. The device of claim 19, wherein the sensor unit is integrated with a separation means for separating particles according to their charges.

33. The device of claim 32, wherein the sensing means consists of a plurality of sensors spaced in the axial direction of the tubular housing.

34. The device of claim 33, wherein each sensor is connected to a measured value evaluation circuit which can be turned on and off by a switch.

35. The device of claim 34, wherein there are a plurality of measured value evaluation circuits, and outputs of the plurality of measured value evaluation circuits are transmitted to a single amplifier.

36. The device of claim 33, wherein an insulating coating is placed over the sensors.

* * * * *